(12) United States Patent
Abehasera

(10) Patent No.: US 11,391,620 B2
(45) Date of Patent: Jul. 19, 2022

(54) DUAL SMART SCALE

(71) Applicant: TRI Innovations, LLC, Hallandale Beach, FL (US)

(72) Inventor: Benyamin Abehasera, Hallandale Beach, FL (US)

(73) Assignee: TRI INNOVATIONS, LLC, Hallandale Beach, FL (US)

(*) Notice: Subject to any disclaimer, the term of this patent is extended or adjusted under 35 U.S.C. 154(b) by 0 days.

(21) Appl. No.: 17/336,453

(22) Filed: Jun. 2, 2021

(65) Prior Publication Data

US 2022/0099478 A1    Mar. 31, 2022

Related U.S. Application Data

(63) Continuation-in-part of application No. 17/033,062, filed on Sep. 25, 2020, now Pat. No. 11,053,040.

(51) Int. Cl.
| | |
|---|---|
| *G01G 21/18* | (2006.01) |
| *A61L 2/10* | (2006.01) |
| *G01D 21/02* | (2006.01) |
| *G01G 21/22* | (2006.01) |
| *G01G 21/28* | (2006.01) |
| *G01G 23/18* | (2006.01) |
| *H04W 4/80* | (2018.01) |
| *G07C 9/37* | (2020.01) |

(52) U.S. Cl.
CPC ............ *G01G 21/28* (2013.01); *A61L 2/10* (2013.01); *G01D 21/02* (2013.01); *G01G 21/22* (2013.01); *G01G 23/18* (2013.01); *A61L 2202/14* (2013.01); *G07C 9/37* (2020.01); *H04W 4/80* (2018.02)

(58) Field of Classification Search
CPC .......... G01G 21/28; G01G 21/22; A61L 2/10; G01D 21/02
See application file for complete search history.

(56) References Cited

U.S. PATENT DOCUMENTS

| | | | |
|---|---|---|---|
| 9,981,790 B1* | 5/2018 | Ost | G01G 19/52 |
| 11,033,645 B1* | 6/2021 | Mora | A61L 2/26 |
| 2012/0003126 A1* | 1/2012 | Engelhard | A61L 9/00 422/121 |
| 2013/0048876 A1* | 2/2013 | Crawford | A61L 2/10 250/492.1 |
| 2018/0177945 A1* | 6/2018 | Sims | A61M 5/16827 |
| 2019/0099509 A1* | 4/2019 | Martz | A61L 2/10 |
| 2020/0349796 A1* | 11/2020 | Gokcebay | G07C 9/00912 |

* cited by examiner

*Primary Examiner* — Kevin Joyner
(74) *Attorney, Agent, or Firm* — Geoffrey Lottenberg; Berger Singerman LLP

(57) ABSTRACT

A dual-scale has a housing placed between an upper scale try and a lower scale tray. The housing contains electronic components including one or more displays, a microcontroller, a sensor array and functional buttons. At least one scale tray includes LEDs for illumination and sanitizing functions. The sensor array includes a scale transducer and humidity, temperature, and pH sensors. A lockable cap is included to cover the scale trays. A biometric sensor provides locking and unlocking functions. A position sensor determines the orientation of the displays. The functions of the electronics can be controlled by an external devices, like a smartphone, through a software application.

19 Claims, 3 Drawing Sheets

DUAL SMART SCALE

CROSS REFERENCE TO RELATED APPLICATIONS

This application is a continuation in part of U.S. patent application Ser. No. 17/033,062, Filed Sep. 25, 2020.

FIELD OF THE INVENTION

The present invention relates to the technical field of digital scales, more particularly to a computer-connectable scale for weighing herbs and other materials.

DETAILED DESCRIPTION

In the following description, for the purposes of explanation, numerous specific details are set forth in order to provide a thorough understanding of the present invention. It will be apparent, however, to one skilled in the art that the present invention may be practiced without some of these specific details. Throughout this description, the embodiments and examples shown should be considered as exemplars, rather than as limitations on the invention. That is, the following description provides examples, and the accompanying drawings show various examples for the purposes of illustration. However, these examples should not be construed in a limiting sense as they are merely intended to provide examples of the invention rather than to provide an exhaustive list of all possible implementations thereof.

Specific embodiments of the invention will now be further described by the following, non-limiting examples which will serve to illustrate various features. The examples are intended merely to facilitate an understanding of ways in which the invention may be practiced and to further enable those of skill in the art to practice the invention. Accordingly, the examples should not be construed as limiting the scope of the invention. In addition, reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" or "in some embodiments" in various places throughout this specification are not necessarily all referring to the same embodiment. Furthermore, the particular features, structures or characteristics may be combined in any suitable manner in one or more embodiments.

Figure 1:
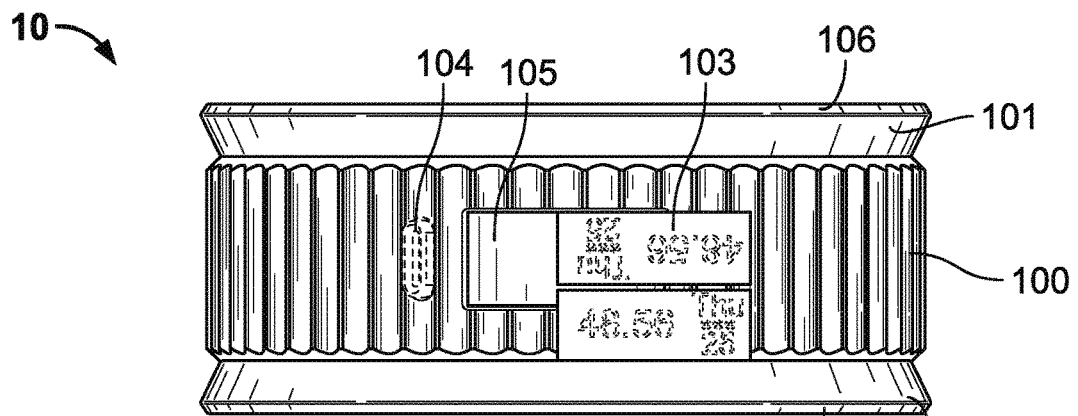
FIG. 1 is a perspective view of the scale.
Figure 2:
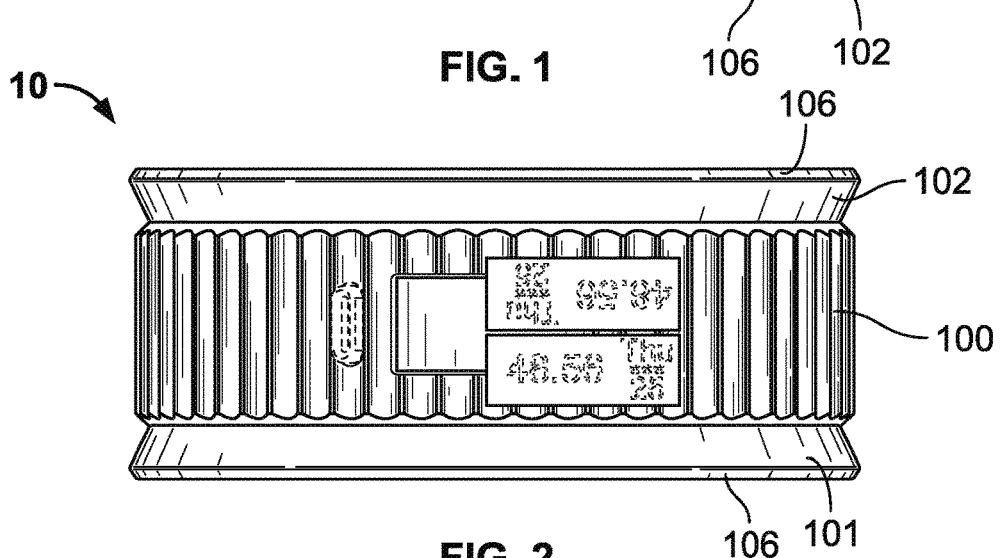
FIG. 2 is a perspective view of the scale in an upside down position.
Figure 3:
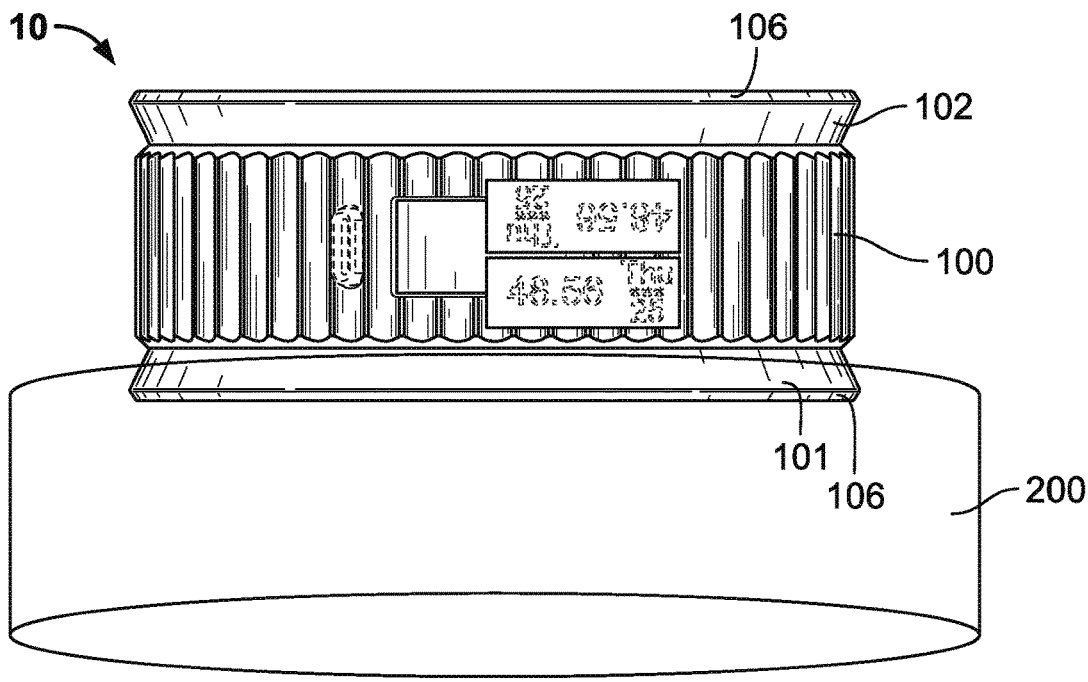
FIG. 3 is an exploded view of the scale with an attachment sleeve.

Referring to FIGS. 1-2, the multi-function scale 10 of the present invention comprises a housing 100 disposed between an upper scale tray 101 and a lower scale tray 102. The housing 100 contains the electronic and other components. In some embodiments, the scale 10 is removably attached to other devices, such as containers, cups, and the like by snap-fit, interference fit, threads, magnetic connection, or the like for ease of use, cleaning, and replacement of parts. With reference to FIG. 3, an attachment sleeve 200 can be employed to attach the scale 10 to other device or elements. In some embodiments, the attachment sleeve 200 comprises a tubular elastic element.

In some use cases the scale 10 is oriented such that the lower scale 102 rests on an underlying surface and the upper scale tray 101 is oriented upward such that items can be weighed on the upper scale tray 101. In other use cases, the scale 10 flipped over such that the upper scale tray 101 rests on an underlying surface and lower scale tray 102 faces upward. Accordingly, the present invention provides a dual-scale arrangement, with each of the upper and lower scale trays comprising a surface for weighing an object placed thereon, for maximum versatility and reorientation of the scale 10 for a variety of uses.

Figure 4:
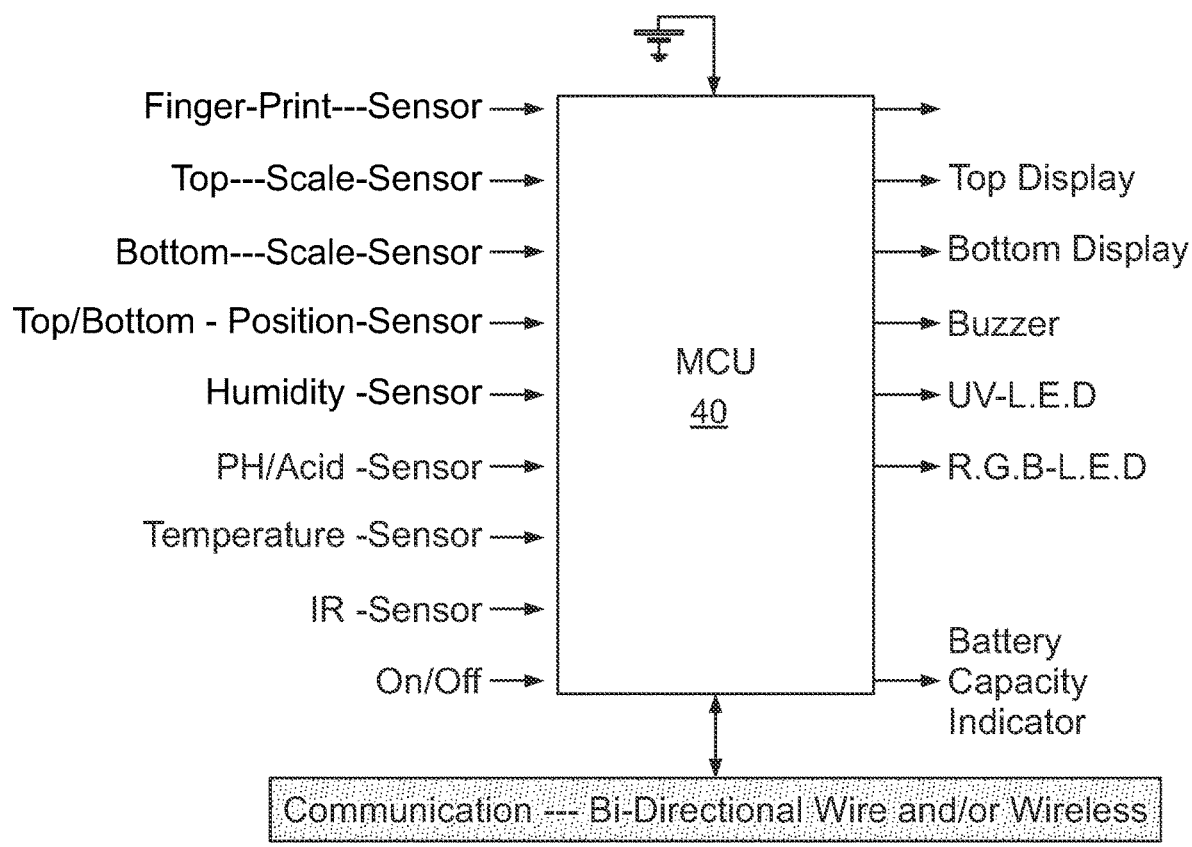
FIG. 4 is a system diagram of the electronic components of the scale.

In some embodiments, the housing 100 includes a power source, such as a rechargeable battery or external power supply, a microcontroller 40 (FIG. 4), one or more displays 103, one or more buttons 104, and a biometric sensor 105. With reference to FIG. 4, microcontroller 40 provides power and communication connectivity for the various system components including a communications device, display(s) 103, and a sensor array (see left side of FIG. 4). In some embodiments the microcontroller 40 comprises a processor (CPU), memory, and control programming for the various input and output peripherals. The communications device may comprise a modem, Wifi chip, a Bluetooth chip, a NFC chip, a Universal Serial Bus (USB) port, or combinations thereof. In some embodiments the communication device is configured to communicate with an external computing device such as a computer or smartphone in order to send and receive data including status information, scale information, and commands. Data transmission can be accomplished through a customized application running on the smartphone or computer.

The one or more displays 103 may each comprise an LED, LCD, OLED, or like displays that can be used to output various information including contents weight, battery status, communications status, and the like. In some embodiments, a single display is employed which can change its orientation based on a position sensor in communication with the microcontroller 40. This allows the display to display content in the correct orientation for the user, regardless of the orientation of the scale. In other embodiments, two displays are employed oriented in opposing directions whereby the position sensor activates the appropriate display depending on the orientation of the scale 10. The display may also include a magnifying lens or cover to increase the visible size of the output of the display to aid in reading by the user. The display(s) can be either flat or curved to match the geometry and shape of the housing 100.

The buttons 104 can be used as an onboard control interface and may be multi-function and programmed to operate different functions based on the number and duration of presses. In some embodiments one or more of the buttons 104 is a multi-touch touch screen for added functionality. In some embodiments, the biometric sensor 105 is configured as a fingerprint sensor which can be pre-programmed with biometric information and function to lock and unlock the scale 10.

The sensor array (left side of FIG. 4) can comprise a multifunction sensor system to interact with the scale trays 101 and 102 and/or to detect and transmit information about the conditions proximate to the scale 10. In some embodiments, the sensor array is functions as a scale transducer and is in physical communication with the upper and lower scale trays to measure the mechanical energy, i.e. the pressure applied to the scale trays by the contents placed thereon, and converts the pressure to an electrical output (e.g. current or voltage differential). In embodiments, two scale transducer, e.g. top scale sensor and bottom scale sensor, are used, with the top scale sensor in communication with the upper scale tray 101 and the bottom scale sensor in communication with the lower scale tray 102. The electrical output at the sensor array is processed into a digital signal by the microcontroller 40 which digital signal can then be outputted on display 103 or through the communications device. Additional sensors of the sensor array include a fingerprint sensor, a position sensor, a humidity sensor, a pH sensor, a temperature sensor, and an IR sensor. Also included in some embodiments is an audible buzzer or alert responsive to various inputs and outputs of the system. The buzzer can be configured to trigger based on predetermined parameters detected by the sensor array, such as a predetermined weight, temperature, humidity, or pH level. A battery indicator may also be provided, which can be shown on the display 103 or through the LED lights 106 described below.

With reference back to FIGS. 1-3, in some embodiments the scale 10 includes one or more LED lights 106 configured as discrete lights or in ring or strip that, in some embodiments, is disposed at or about either or both of the scale trays. In some embodiments the lights 106 is configured with one or more LEDs (light emitting diodes) configured to emit light in the UVC (100-280 nm) range in order to sanitize areas or spaces proximate to the scale 10. In some embodiments, the lights 106 comprises one or more RGB LEDs, the color of which are user-selectable through the electronics of the scale 10. The lights 106 can be placed in electrical communication with the microcontroller 40 and, therefore, the communications device. In some embodiments, the output of the lights 106 is controlled by one or more switches including a momentary switch (toggle/title, or depressible) or a latch switch. Frequency adjustments of the light are controlled by one or more MOSFETs which are used to adjust and control the (pulse width modulation) PWM frequency and interval of the lights.

In some embodiments, the scale 10 includes safety and locking features that function by way of the various system components. For example, as noted the scale 10 includes a biometric sensor 105 or other biometric lock system that is configurable via the customized application. In some embodiments, the communications device can function as a locking system such as, for example, a proximity-base locking system via NFC or Bluetooth.

Figure 5:
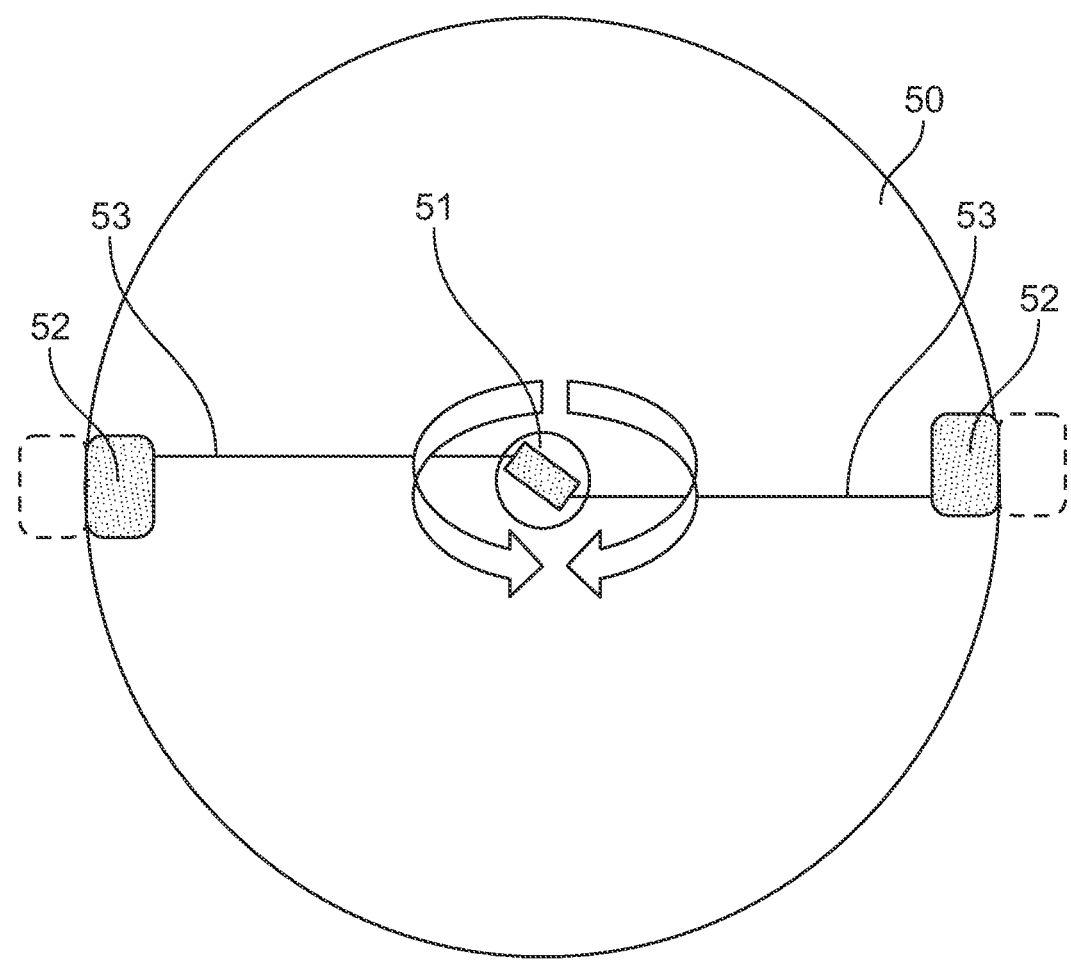
FIG. 5 is a schematic of the locking mechanism of the scale.

With reference to FIG. 5, in some embodiments the scale 10 includes a cap 50 which is received over either or both of the scale. The cap 50 includes a bi-lateral locking mechanism comprising a rotating handle 51 which is attached to two linkages 53 offset from one another and extending radially outward from the rotating handle 51. The distal end of each linkage 53 includes a stop 52 which is moveable from an unlocked position (solid lines) to a locked position (dashed lines). In the locked position, the stops 52 press against the scale 10 to retain the cap on the scale 10. The handle 51 can be operated by electronic or manual means and can be configured to be locked and unlocked by the biometric sensor 105.

As noted above, the container includes connectivity features such that the communications device can communicate with an outboard smartphone or computer for added functionality. In some embodiments the container is "app-enabled" and works in conjunction with control and notification software. The user can utilize an application running on a smartphone or computer to obtain information from the container such as weight, battery status, temperature, humidity, or the like. In some embodiments, each time the container is turned on either or both of the scale trays obtains a weight measurements and stores corresponding weight data in the memory of the microcontroller. Then, each time of the user loads the application on his computing device, the stored weight information is automatically synchronized to the application.

It is to be noticed that the term "comprising," used in the claims, should not be interpreted as being limitative to the means listed thereafter. Thus, the scope of the expression "a device comprising means A and B" should not be limited to devices consisting only of components A and B. It means that with respect to the present invention, the only relevant components of the device are A and B. Put differently, the terms "including", "comprising" and variations thereof mean "including but not limited to", unless expressly specified otherwise.

Similarly, it is to be noticed that the term "coupled", also used in the claims, should not be interpreted as being limitative to direct connections only. Thus, the scope of the expression "a device A coupled to a device B" should not be limited to devices or systems wherein an output of device A is directly connected to an input of device B. It means that there exists a path between an output of A and an input of B which may be a path including other devices or means.

The enumerated listing of items does not imply that any or all of the items are mutually exclusive, unless expressly specified otherwise. The terms "a", "an" and "the" mean "one or more", unless expressly specified otherwise.

Elements of the invention that are in communication with each other need not be in continuous communication with each other, unless expressly specified otherwise. In addition, elements of the invention that are in communication with each other may communicate directly or indirectly through one or more other elements or other intermediaries.

One skilled in the art will appreciate that the present invention can be practiced by other than the above-described embodiments, which are presented in this description for purposes of illustration and not of limitation. The specification and drawings are not intended to limit the exclusionary scope of this patent document. It is noted that various equivalents for the particular embodiments discussed in this description may practice the invention as well. That is, while the present invention has been described in conjunction with specific embodiments, it is evident that any alternatives, modifications, permutations and variations will become apparent to those of ordinary skill in the art in light of the foregoing description. Accordingly, it is intended that the present invention embrace all such alternatives, modifications and variations as fall within the scope of the appended claims. The fact that a product, process or method exhibits differences from one or more of the above-described exemplary embodiments does not mean that the product or process is outside the scope (literal scope and/or other legally-recognized scope) of the following claims.

What is claimed is:
1. A scale, comprising:
 a housing disposed between an upper scale tray and a lower scale tray, each of the upper scale tray and the lower scale tray comprising a surface configured to weigh an object placed thereon;
 the housing including a microcontroller, a display, and a sensor array;
 wherein the sensor array comprises a first scale transducer and second scale transducer, each of the first and second scale transducers in electrical communication with the microcontroller and the first scale transducer in communication with the upper scale tray and the second scale transducer in communication with the lower scale tray.

2. The scale of claim 1, wherein the display is in electrical communication with the microcontroller.

3. The scale of claim 2, including a position sensor in electrical communication with the microcontroller, the position sensor configured to change the orientation of information shown on the display.

4. The scale of claim 2, including a position sensor in electrical communication with the microcontroller, the position sensor configured to activate the display depending on the orientation of the scale.

5. The scale of claim 1, including a biometric sensor in electrical communication with the microcontroller.

6. The scale of claim 1, including one or more buttons in electrical communication with the microcontroller.

7. The scale of claim 1, including a communications device comprising a modem, Wifi chip, a Bluetooth chip, a NFC chip, a Universal Serial Bus (USB) port, or combinations thereof in electrical communication with the microcontroller.

8. The scale of claim 7, wherein the communication device is configured to communicate with an external computing device including a computer or smartphone in order to send and receive data including status information, scale information, temperature information, humidity information, pH level information, and commands.

9. The scale of claim 1, including one or more light-emitting-diodes (LEDs).

10. The scale of claim 9, wherein the LEDs are configured in a ring surrounding the perimeter of at least one of the upper scale tray and lower scale tray.

11. The scale of claim 9, wherein the LEDs emit light in the UVC range of 100-280 nm.

12. The scale of claim 9, wherein the LEDs are controlled by a MOSFET to adjust the pulse width modulation thereof.

13. The scale of claim 1, wherein the sensor array comprises a temperature sensor, a humidity sensor, a pH sensor or combinations thereof.

14. The scale of claim 1, including one or more buttons in electrical communication with the microcontroller.

15. The scale of claim 1, including a cap received over at least one of the upper scale tray and lower scale tray.

16. The scale of claim 15, the cap including a locking mechanism.

17. The scale of claim 16, wherein the locking mechanism is trigged by a biometric sensor, the biometric sensor in electrical communication with the microcontroller.

18. The scale of claim 1, including an attachment sleeve to facilitate attachment of the scale to an external element.

19. A scale, comprising:
    a housing disposed between an upper scale tray and a lower scale tray, each of the upper scale tray and the lower scale tray comprising a surface configured to weigh an object placed thereon;
    the housing including a microcontroller, a display, and a sensor array;
    wherein the sensor array comprises a scale transducer in electrical communication with the microcontroller and each of the upper scale tray and the lower scale tray; and
    one or more light-emitting-diodes (LEDs), wherein the LEDs are controlled by a MOSFET to adjust the pulse width modulation thereof.

* * * * *